United States Patent [19]

Simons et al.

[11] Patent Number: 4,489,723
[45] Date of Patent: Dec. 25, 1984

[54] SWIMMING APPARATUS

[76] Inventors: Elliot Simons, 8 River View Pl., North Weymouth, Mass. 02191; Robert Boulos, 51 Broad Reach, North Weymouth, Mass. 02190

[21] Appl. No.: 593,363

[22] Filed: Mar. 26, 1984

Related U.S. Application Data

[63] Continuation-in-part of Ser. No. 494,710, May 16, 1983, , which is a continuation-in-part of Ser. No. 467,690, May 28, 1981, Pat. No. 4,401,118.

[51] Int. Cl.³ ............................................ A61M 16/00
[52] U.S. Cl. ...................... 128/207.16; 207.17/207.14; 207.17/136
[58] Field of Search ............... 128/136, 207.14, 207.15, 128/207.16, 207.17, 201.11, 203.11, 202.28, 200.26; 604/101, 332, 334, 338, 336, 341, 351, 352

[56] References Cited

U.S. PATENT DOCUMENTS

| 1,835,757 | 12/1931 | Burchett | 128/207.17 |
| 2,491,647 | 12/1949 | Colavita | 128/207.14 |
| 3,518,989 | 7/1970 | Seeler | 128/203.11 |
| 3,889,688 | 6/1975 | Eamkaow | 128/207.15 |
| 3,920,009 | 11/1975 | Olsen | 128/207.14 |
| 4,332,245 | 6/1982 | Boone | 128/207.14 |

FOREIGN PATENT DOCUMENTS 189504 4/1957 Fed. Rep. of Germany ......................... 128/201.11

Primary Examiner—Richard J. Apley
Assistant Examiner—Harry J. Macey
Attorney, Agent, or Firm—Wolf, Greenfield & Sacks

[57] ABSTRACT

A swimming apparatus that permits an individual with a laryngectomy to be able to swim. The apparatus comprises a mouthpiece, a throat sealing member and an air tube intercoupling the mouthpiece and sealing member. The sealing member is securely disposed to cover and seal about the throat stoma while having an opening to permit air passage to the throat. The mouthpiece is controlled by the swimmer as a valve to control airflow through the unobstructed air tube. Also included are first and second valves associated with the air tubes, a first valve being positioned at the mouthpiece and the second valve being disposed intermediate the ends of the air tube. The first valve is a one way valve permitting air flow through the air tube on an inhalation. The second valve is also a one way valve permitting air exhaust from the air tube during exhalation. Also, in accordance with the invention there is provided about the sealing member, an inflatable air chamber adapted to provide controllable sealing of the sealing member about the throat stoma.

20 Claims, 20 Drawing Figures

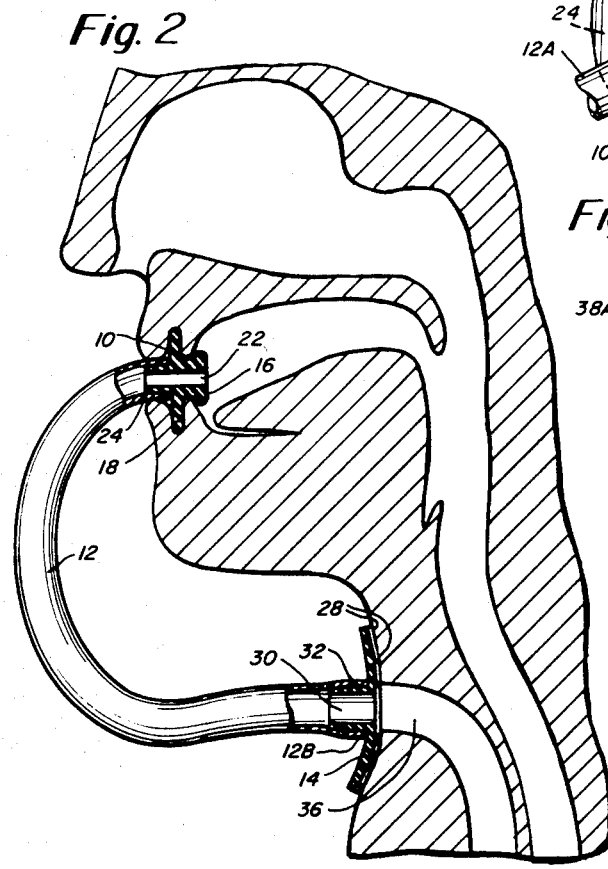
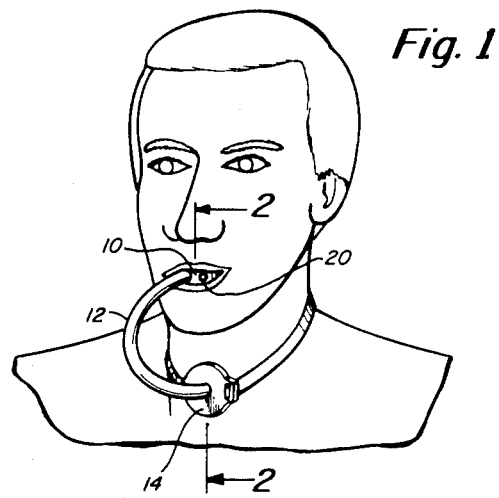
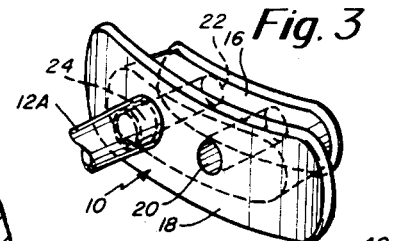
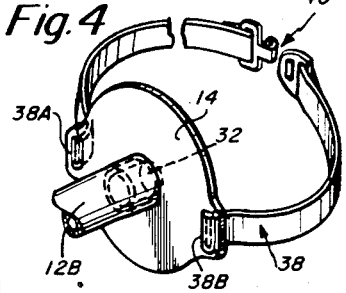
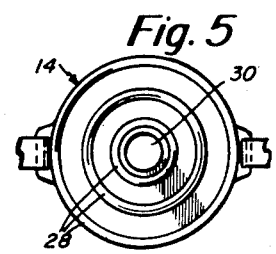

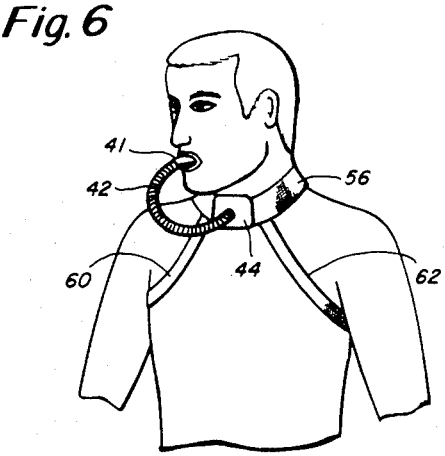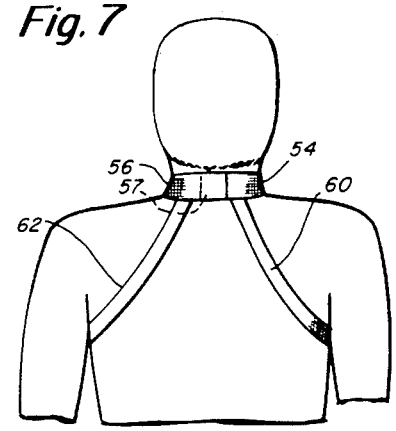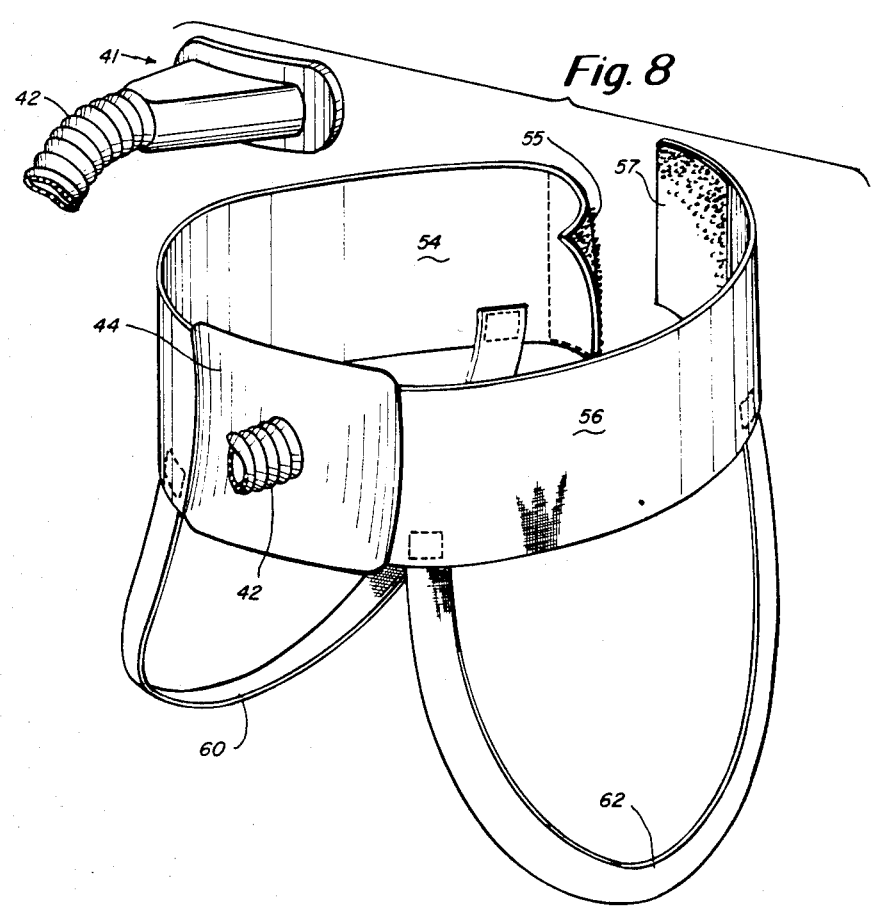

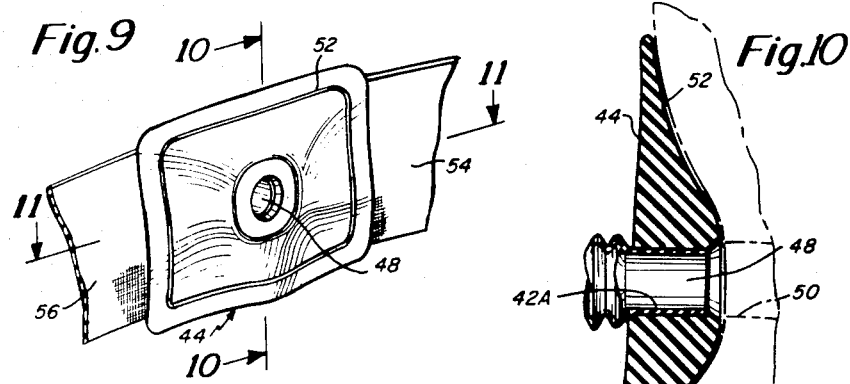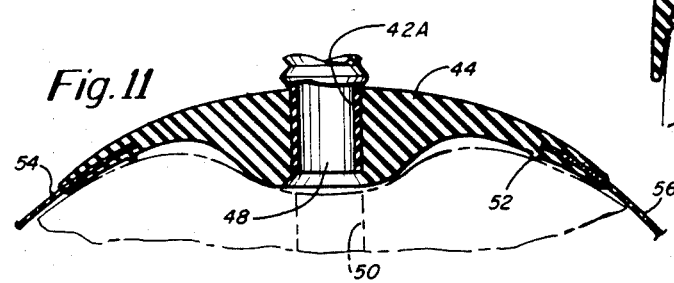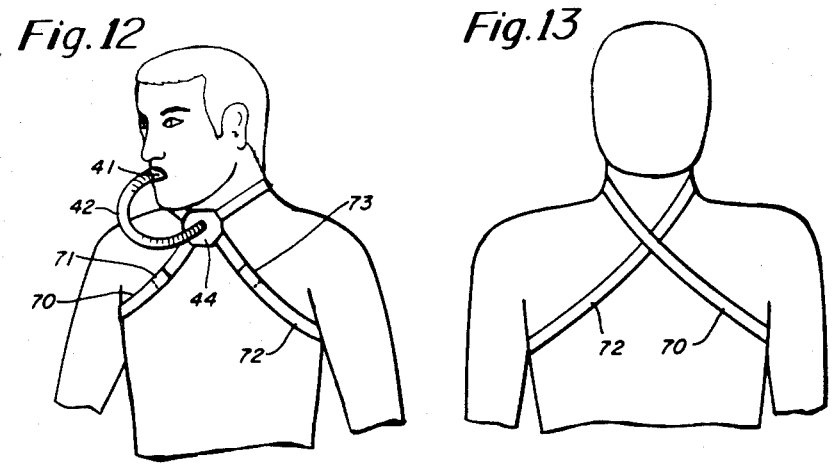

SWIMMING APPARATUS

RELATED APPLICATION

This application is a continuation-in-part of application Ser. No. 494,710 filed May 16, 1983 which in turn is a continuation-in-part of application Ser. No. 467,690 filed May 28, 1981 and now U.S. Pat. No. 4,401,118.

BACKGROUND OF THE INVENTION

The present invention relates in general to a swimming apparatus, and more particularly to a swimming apparatus particularly adapted for use by a individual with a laryngectomy so as to enable that person to swim.

An individual that has had a laryngectomy is not able to enjoy swimming or other water activities because of the absence of control of air flow through the throat stoma. It is very unsafe to attempt swimming particularly where water can easily enter through the throat stoma.

Accordingly, it is an object of the present invention to provide an apparatus which will permit an individual with a laryngectomy to be able to swim safely.

Another object of the present invention is to provide a swimming apparatus in accordance with the preceding object and which is comfortable to wear, easy to attach to the swimmer, and adaptable for use by swimmers of virtually any age.

Still aother object of the present invention is to provide a swimming apparatus in accordance with the preceding objects and which has means for simplifying inhalation and exhalation.

A further object of the present invention is to provide a swimming apparatus which is characterized by improved sealing of the apparatus about the throat stoma. This object is satisfied in accordance with the present invention by means of the use of a controllable inflatable air chamber.

SUMMARY OF THE INVENTION

To accomplish the foregoing and other objects of this invention there is provided a swimming apparatus which is used to enable a person having a laryngectomy or the like to swim safely. This apparatus comprises an elongated unobstructed air tube, a mouthpiece means at one end of the air tube having an air passage communicating with the air tube to enable air passage between the air tube and the person's mouth and a relatively flat sealing member having means forming a water tight seal about the throat stoma. The sealing member also has an air passage and means are provided securing the other end of the air tube to the sealing member enabling air passage between the air tube and the person's throat. A means is provided for holding the sealing member in good sealing relationship to the throat about the throat stoma whereby the person can control air flow in alternate directions corresponding to inhalation and exhalation through the air tube by interaction of the mouth and mouthpiece. This interaction of the mouth and mouthpiece essentially forms a valve for controlling air flow via the air tube during both inhalation and exhalation. In one embodiment described herein the mouthpiece includes a vent adapted to be blocked and unblocked by interaction of the mouth with the vent to control air flow and also selectably block air flow to enable the swimmer to hold his or her breath. The air tube is described as either having a circular cross section and being in the form of a plastic tube or could be a more flexible tube such as one having a pleated-configuration. Also, it is preferred that the sealing member be contoured to fit to the person's throat. A throat mold could be made so that the sealing member is personally fitted to the person that will be using it. The means for forming a water tight seal about the throat stoma may comprise a sealing ridge which is disposed about the periphery of the throat stoma. The means for holding the sealing member preferably includes a strap arrangement including in one embodiment a neck strap and associated fastener and in another embodiment both neck and arm straps. The arm straps have been found to be of advantage in that with the neck strap alone the sealing member may tend to ride up and thus the sealing member is more positively positioned by means of both a neck strap and arm strap. There is also provided valve means associated with the aforementioned air tube. Both of these valve means are preferably one-way valves. The first one of the valves is disposed adjacent to the mouthpiece and is operable during inhalation permitting air in the mouth to be passed by the way of this first valve via the air tube into the throat. The second valve is disposed along the air tube between the mouthpiece and sealing member. This second valve is operable during exhalation to permit air to be directly exhaled from the air tube rather than having to pass into the mouth and exhale from the mouth. In accordance with the present invention, there is provided a means by which the sealing member is maintained in good sealing relationship to the throat about the throat stoma. This is provided in accordance with the invention by a controllably inflatable air chamber, the air pressure into which may be controlled so as to provide the proper sealing relationship of the sealing member against the throat and about the throat stoma.

BRIEF DESCRIPTION OF THE DRAWINGS

Numerous other objects, features and advantages of the invention should now become apparent upon the reading of the following detailed description taken in conjunction with the accompanying drawings in which:

FIG. 1 shows a first embodiment of the present invention as positioned on a user;

FIG. 2 is a cross-sectional view taken along line 2—2 of FIG. 1 showing the air passage communication between throat and mouth;

FIG. 3 is a fragmentary view showing the mouthpiece;

FIG. 4 is a fragmentary view showing the sealing member and associated strap;

FIG. 5 is a rear view of the sealing member showing the means for facilitating sealing to the throat about the throat stoma;

FIG. 6 is a front view of an alternate embodiment of the invention;

FIG. 7 is a rear view of the embodiment of FIG. 6 showing the rear strap arrangement;

FIG. 8 is a perspective view showing the mouthpiece and the sealing member and associated straps;

FIG. 9 shows a further detail on the inside of the sealing member;

FIG. 10 is a cross-sectional view taken along line 10—10 of FIG. 9;

FIG. 11 is a cross-sectional view taken along line 11—11 of FIG. 9;

FIG. 12 is a front view of still another embodiment of the invention employing a different strap configuration;

FIG. 13 is a rear view of the strap arrangement of FIG. 12; and

DETAILED DESCRIPTION

Figure 14:
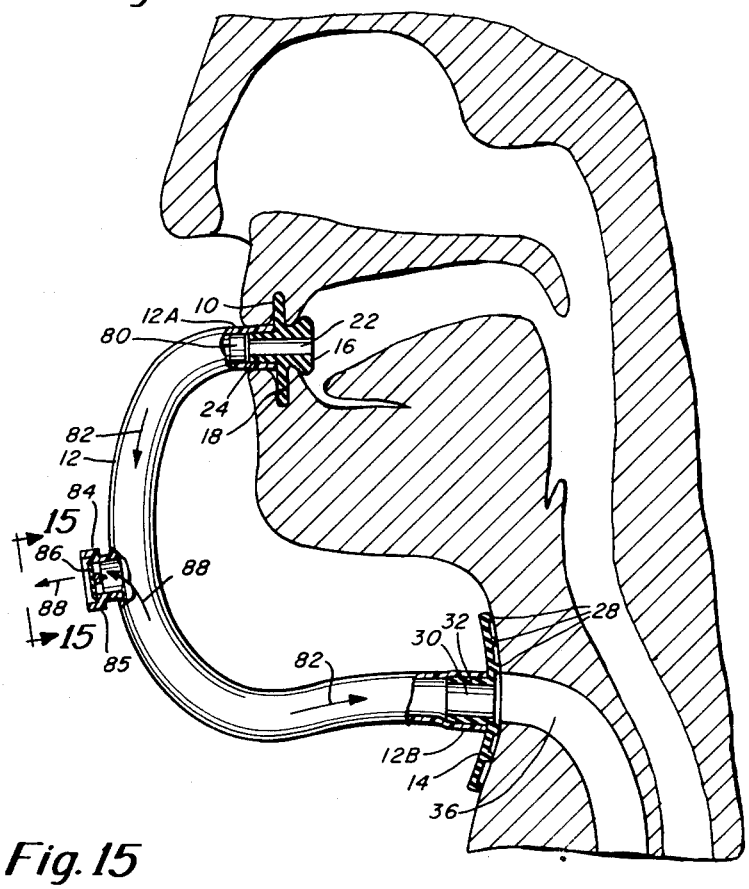
FIG. 14 shows an embodiment of the present invention in a view similar to the view of FIG. 2 and showing the use of valve means in association with the air tube.
Figure 15:
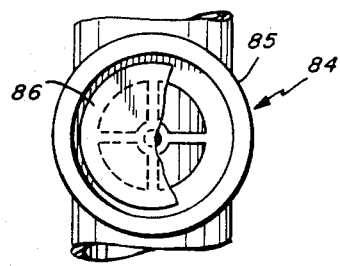
FIG. 15 is a view taken along line 15—15 of FIG. 14 showing further details of one of the valves.

The swimming apparatus of the present invention enables a person having had a laryngectomy to be able to swim. A first embodiment of the invention is shown in FIGS. 1-5, a second embodiment in FIGS. 6-11 and an alternate strap arrangement in FIGS. 12 and 13. Still another embodiment of the present invention is illustrated in FIGS. 14 and 15 employing valve means for facilitating and simplifying inhalation and exhalation. Yet another embodiment of the present invention is illustrated in FIGS. 16-19 illustrating an improved means for sealing the apparatus about the throat stoma.

The first embodiment in FIGS. 1-5 shows the swimming apparatus in operative position on the person. This apparatus comprises a mouthpiece 10, an elongated unobstructed air tube 12, and a flat sealing member 14. The mouthpiece 10 has an inner side 16 and an outer flange plate 18. The plate 18 is adapted to fit between the mouth and the teeth in the normal manner of a mouthpiece. Extending through the mouthpiece is a passage 20 forming a vent which can be covered and uncovered by the tongue to control air flow therethrough into and out of the mouth. Adjacent to the passage 20 is another passage 22 having at its outer end a circular flange 24 adapted to receive the end 12A of the air tube 12, as clearly depicted in FIG. 3.

As indicated in FIG. 5, the sealing member 14 has a series of circular sealing ridges 28. There is also provided a hole 30 at the center of the sealing member 14 and having on the outer side thereof a circular flange 32 adapted to receive the other end 12B of the unobstructed air tube 12, as depicted in FIG. 4. The ends 12A and 12B of the tube 12 may be secured to the respective mouthpiece and sealing member by an adhesive material or some type of a clamp could be used. Also, Vaseline may be used on the throat facing surface of the sealing member to provide a good seal against the throat with the passage 30, properly in line with the throat stoma 36.

The sealing member is held in tight relationship to the throat about the throat stoma by means of a strap 38 secured at ends 38A and 38B to the sealing member. The strap 38 also has a fastening means such as the means 40 shown in FIG. 4.

In the embodiment of FIGS. 1-5 during inhalation air passes through the vent 20 into the mouth where it is conveyed by the air tube to the throat stoma. In order to provide proper air passage and to prevent water from entering the throat stoma the strap holds the sealing member tight against the throat and the sealing ridges assist in providing a water tight seal. The breath may be held by sealing the vent 20 to hold the air in the lungs. Exhalation occurs through the air tube into the mouth and out of the vent 20.

In accordance with the invention the mouthpiece may be replaced by a nose piece in which case the breathing is controlled through the nose rather than the mouth. However, the mouthpiece version is preferred.

A second embodiment of the invention is shown in FIGS. 6-11 including a preferred strap construction. The apparatus comprises a mouthpiece 41, and elongated unobstructed tube 42, and molded sealing member 44. In this embodiment the air tube 42 has a pleated construction to enhance flexibility. In this embodiment the sealing member 44 is constructed preferably of a silicone (RTV) rubber and is molded to the configuration of the person. In this way the sealing member will fit tightly against the throat in alignment with the throat stoma. FIGS. 10 and 11 show the end 42A which is a straight end section, embedded within a passage in the sealing member 44. This provides a passage 48 that is adapted to be in line with the throat stoma 50. This embodiment also has a sealing ridge 52 about its perimeter as depicted in FIG. 9. Vaseline or the like lubricant may also be employed between the sealing member 44 and the throat surface. Also, a resilient rubber-like material may be used as a seal secured to the inner surface of the sealing member and disposed between the sealing member and the throat. Again, the purpose of any lubricant or resilient material along with the ridge 52 is to provide a water tight seal about the throat stoma. By contouring the inner surface of the sealing member to match that of the person's throat this also assures a water tight seal. The sealing member is held in place by means of a main strap comprising strap pieces 54 and 56 each having respective Velcro ends 55 and 57 to form a fastening means for the upper strap. There are also provided secured from the upper strap, lower straps 60 and 62 adapted to be placed under the arms as clearly depicted in FIGS. 6 and 7.

The throat stoma is generally located at a low position on the neck and thus with the use of only an upper strap, the sealing member may tend to ride up the throat and not properly provide a water tight sal. However, with the use of the two lower straps 60 and 62 there is sufficient downward force on the upper strap to maintain the sealing member in proper alignment with the throat stoma.

FIGS. 12 and 13 show respective front and rear views of a person with the swimming apparatus of this invention in a slightly different embodiment. In this version the mouthpiece, air tube and sealing member may be identical to that shown in FIGS. 6 and 7. Thus, as indicated in FIG. 12, there is shown the mouthpiece 41 interconnected by the air tube 42 to the sealing member 44. In this embodiment there are provided a pair of criss-cross straps 70 and 72. Each of these straps connect at one end to the sealing member 44 and extend downwardly under the armpit and crossing to the other side of the body in the rear as shown in FIG. 13 to pass over the shoulder near the neck for fastening to an opposite side of the sealing member 44. Each of these straps may be provided with, for example, a Velcro fastener shown in FIG. 12 as fasteners 71 and 73 associated respectively with the straps 70 and 72.

With regard to the first embodiment described herein, it is noted that a vent 20 is used. In the latter two embodiments, no vent is provided but instead the mouth can be parted from the mouthpiece to enable air to enter and leave the mouth.

FIGS. 14 and 15 illustrate another embodiment of the present invention in which exhalation is possible directly from the air tube. In the previous description, in FIG. 2 exhaled air passed to the mouth and was then exhaled therefrom. In the embodiment shown in FIGS. 14 and 15 the exhalation can occur directly by way of valve means from the air tube. This substantially simplifies the functional operation and furthermore reduces the chance of getting water into the mouth and possibly into the air tube.

In FIGS. 14 and 15 the same reference characters are used as were previously used in connection with the description of FIGS. 1-5. Thus, in FIGS. 14 and 15 the apparatus comprises a mouthpiece 10, an elongated air tube 12, and a flat sealing member 14. The mouthpiece 10 has an inner side 16 and an outer flange plate 18. The plate 18 is adapted to fit between the mouth and the teeth in the normal manner of a mouthpiece. Extending through the mouthpiece may be a passage 20 forming a vent which can be covered and uncovered by the tongue to control air flow therethrough principally into the mouth. Adjacent to the passage 20 is another passage 22 having at its outer end a circular flange 24 adapted to receive the end 12A, of the air tube 12, as clearly depicted in FIG. 14.

The sealing member 14 preferably has a series of circular sealing ridges 28. There is also provided a hole 30 at the center of the sealing member 14 and having on the outer side thereof a circular flange 32 adapted to receive the other end 12B of the air tube 12. The ends 12A and 12B of the tube 12 may be secured to the respective mouthpiece and sealing member by an adhesive material or some type of a clamp could be used. Also, Vaseline may be used on the throat facing surface of the sealing member to provide a good seal against the throat with the passage 30 properly in line with the throat stoma 36 as depicted in FIG. 14. The sealing member is held in tight relationship above the throat stoma by means of a strap arrangement discussed previously in connection with previous embodiments of the invention that have been described herein.

In this embodiment there is also provided a first valve 80 which may be a conventional one way valve not shown in detail 14 in FIG. 14. However, this valve may be of the general type illustrated in some more detail in FIG. 15 including, for example, a body and a displaceable flap. In FIG. 14 the arrows 82 illustrative the direction of air flow permitted through the valve 80. The valve 80 does not permit air flow from the air tube back into the mouth because it is a one way valve. Thus, on inhalation air is passed into the mouth such as by parting the mouthpiece or if the vent 20 is used by means of the vent 20. The air then passes by way of the one way valve 80 into the air tube in the direction of flow indicated by the arrows 82 and from there to the throat and lungs.

As far as exhalation is concerned there is provided a second valve 84 connected along the air tube 12. FIG. 15 shows somewhat more detail of the valve 84 which includes a body 85 and a valve flap 86. A valve flap may be a relatively thin plastic membrane which is positioned to deflect from the body 85 when air flows in one direction and is adapted to deflect toward the body when air flows in the opposite direction to provide a seal. In FIG. 14 the arrows 88 indicate the direction of air flow during exhalation from the lungs and throat to the air tube 12 and from therethrough the one way valve 84. During exhalation the air will not pass to the valve 80 because this is a one way valve and thus all of the air will be exhausted at the valve 84 essentially from the air tube rather than passing into the person's mouth. Also, during inhalation the valve 84 is essentially closed as the path of least resistance to air flow is through the tube and into the lungs.

FIGS. 16–19 now illustrate a further embodiment of the present invention as covered by the claims attached hereto. In this embodiment of the invention, the same reference characters are used to identify previous parts of the apparatus referred to in FIGS. 1-15. Thus, in FIGS. 16–19 there is shown a swimming apparatus in operative position on a person. This Apparatus comprises a mouthpiece 10, an elongated unobstructed air tube 12 and a flat sealing member 14. The mouthpiece 10 may be of the type illustrated in FIG. 1 or may be of the type illustrated in FIG. 14. For the sake of simplicity in describing this embodiment, the valve means illustrated in FIGS. 14 and 15 has not been shown. However, it is understood that the air chamber sealing concepts of FIGS. 16–19 may be implemented with the use of the valve means illustrated in FIGS. 14 and 15, for example. With regard to the sealing member 14, this may be generally of the type illustrated in FIG. 9 and may be contoured in the manner illustrated in FIGS. 9-11 from this application. The sealing member 14 is preferably constructed of a silicone rubber. Although, by contouring the sealing member, it provides a more effective seal, in accordance with the present invention, it has been found desirable to provide additional controllable sealing and this is provided in accordance with the present invention by the use of an air chamber 90. The air chamber 90 is disposed in front of the sealing member 14 and includes in general a front piece 91 illustrated in FIG. 17 and a rear piece 92 also illustrated in FIG. 17.

Figure 18:
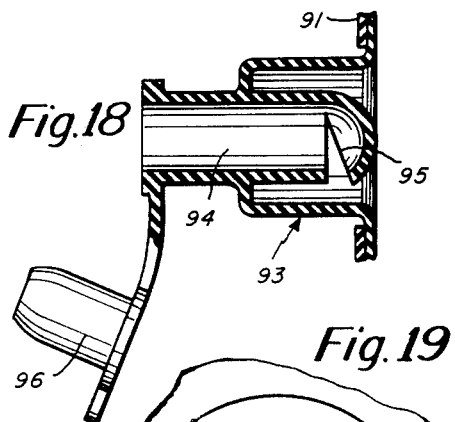
FIG. 18 is a further detailed cross-sectional view taken along 18—18 of FIG. 17.

The air chamber or air bag 90 is totally sealed and the only air input and exit port is by means of the valve 93, the details of which is illustrated in FIG. 18. The flap valve 93 has an elongated passage 94 with a spherical end that is partially cut at 95. FIG. 18 illustrates the valve in solid in its closed position and also illustrates the valve in phantom in its open position. The valve is moved to its open position by means of inserting a stick or pencil into the passage 94 to deflect the end member into the position indicated in phantom so as to open the valve. It is also noted in FIG. 18 that there is provided a sealing cap 96.

In use, before the user attaches the swimming aid around the throat stoma, the air chamber 90 is inflated to a desired level of inflation. The air is forced under simple mouth pressure through the passage 94 and into the air chamber. The pressure inside of the air chamber maintains the valve closed and the valve is only opened by means of inserting a pencil or the like into the passage 94 to deflect the end of the passage and open the slit at 95 to let the pressurized air release.

Once the air chamber 90 is inflated to the proper pressure for that particular user, then the cover 96 is used simply as a precautionary measure to assure that the pressure is maintained in the air chamber. For any one particular user, the air pressure should not have to be changed once it is adjusted to the right pressure for that particular user.

Figure 19:
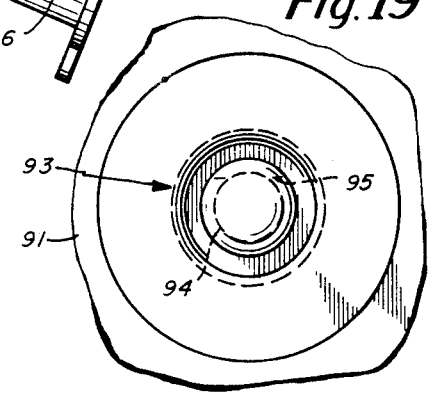
FIG. 19 illustrates the back side of the swimming aid apparatus.
Figure 20:
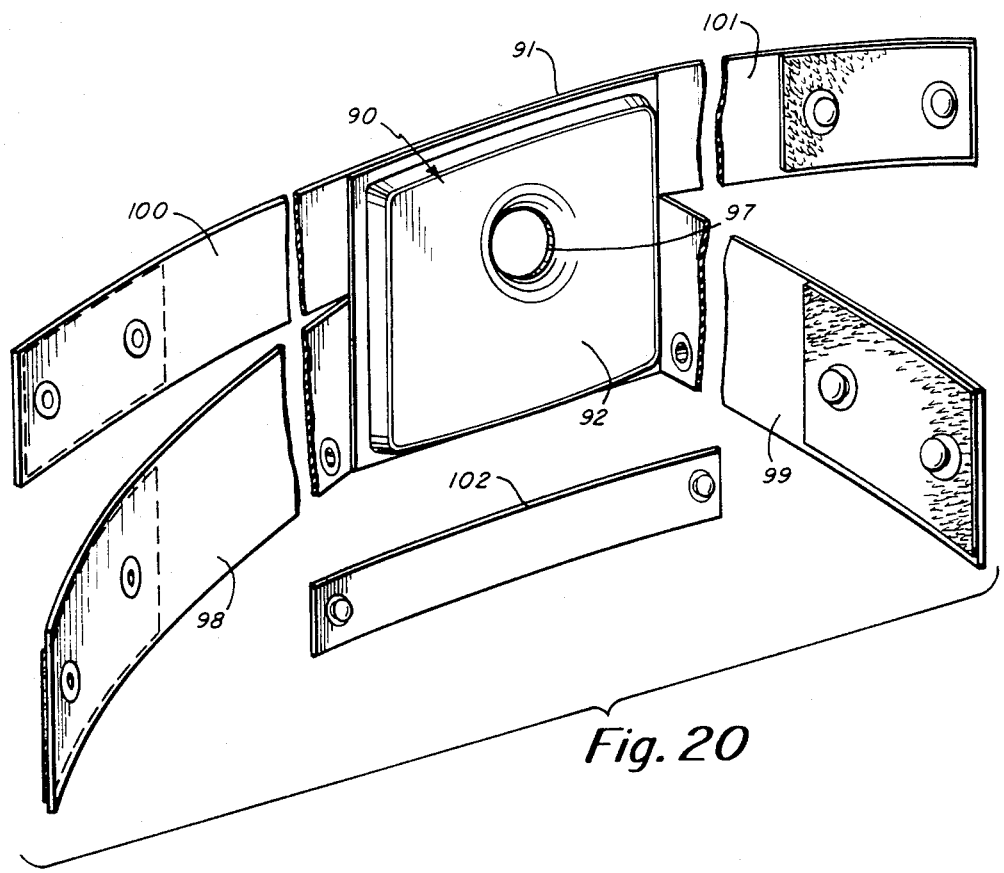
FIG. 20 is a further back side perspective of the swimming aid apparatus.

FIG. 19 illustrates the rear piece 92 that is used to form part of the air chamber 90. It is noted that the rear piece 92 has a hole 97. The piece 92 is glued about the hole 97 and is also glued about its periphery so as to properly form the air chamber. The hole 97 is simply for receiving the sealing member 14.

Figure 16:
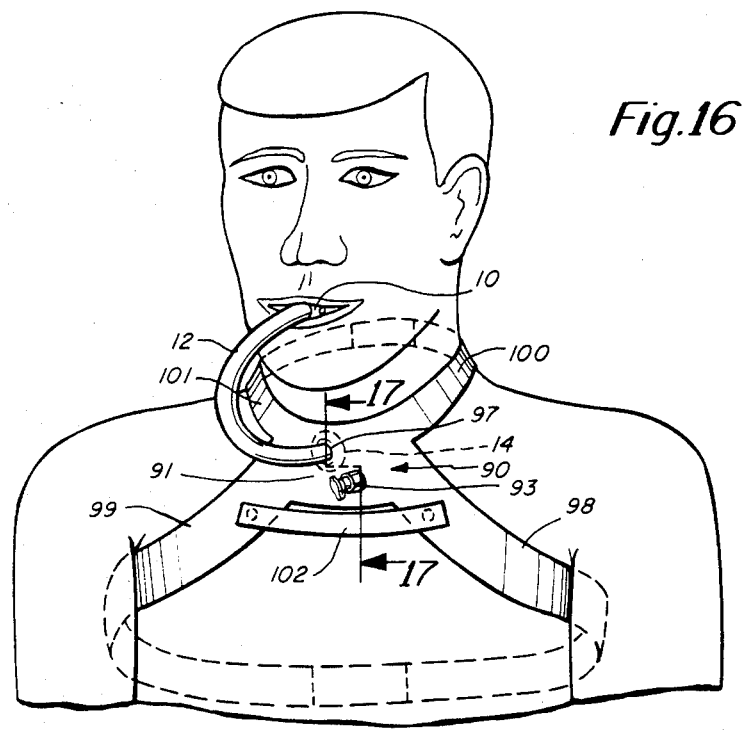
FIG. 16 shows a further embodiment of the present invention employing a controllably inflatable air chamber for providing improved sealing against the throat.
Figure 17:
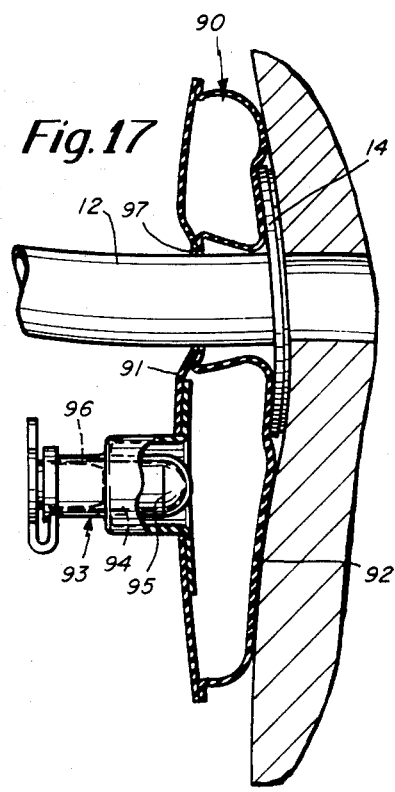
FIG. 17 is a view as taken along line 17—17 of FIG. 16 showing further details of the air chamber.

FIG. 19 also illustrates the strap arrangement that is employed, which is similar to the strap arrangement previously shown in connection with FIGS. 12 and 13, for example. However, in this embodiment, the lower straps 98 and 99 (see also FIG. 16) extend under the arms and about the user's body. As illustrated, snaps and/or Velcro fasteners may be used for securing this lower strap in place. There is also provided an upper strap comprised of strap pieces 100 and 101. This strap is adapted to fit about the user's neck as illustrated in FIG. 16. This strap also may be provided with Velcro and/or snap fasteners. There is also preferably provided one additional short strap illustrated in phantom in FIG. 19 and illustrated in solid in FIG. 16. This is the strap 102 shown in FIG. 16 as extending between the top ends of straps 98 and 99. This strap is used for providing additional sealing and is used depending upon the user's chest size.

Having described a limited number of embodiments of this invention, it should now be apparent to those skilled in the art that numerous other embodiments are contemplated as falling within the scope of this invention. For example, the mouthpiece may be substituted in another embodiment by a nose piece. Also, the mouthpiece may be simply formed by the end of the air tube rather than the special construction of mouthpiece particularly described herein.

What is claimed is:

1. A swimming apparatus used to enable a person having a laryngectomy or the like to safely swim, said apparatus comprising; an elongated unobstructed air tube, a mouthpiece means at one end of the air tube tube having an air passage communicating with the air tube to enable air passage between the air tube and a person's mouth, a relatively flat sealing member having means forming a water tight seal about the throat stoma, said sealing member also having an air passage, means securing the other end of the air tube to the sealing member enabling air passage between the air tube and person's throat, and means holding the sealing member in water tight sealing relationship to the throat about the throat stoma, said means holding the sealing member comprising both a fastening means coupled to the sealing member for securing the sealing member to the person and a means defining a controllable inflatable air chamber attached to the apparatus in front of and adjacent to the sealing member for maintaining the sealing member in a water tight position about the throat stoma, whereby the person controls air flow in alternate directions corresponding to inhalation and exhalation through the air tube by interaction of the mouth and mouthpiece.

2. A swimming apparatus as set forth in claim 1 wherein said mouthpiece blocks substantially the whole mouth but including a vent adapted to be blocked and unblocked by interaction of the tongue with the vent to control air flow and also selectively block air flow as in holding the breath.

3. A swimming apparatus as set forth in claim 1 wherein said air tube is a circular cross-section plastic tube.

4. A swimming apparatus as set forth in claim 1 wherein said air tube has a pleated configuration to enhance its flexibility.

5. A swimming apparatus as set forth in claim 1 wherein said sealing member is molded to the contour of the person's throat.

6. A swimming apparatus as set forth in claim 1 wherein said means forming a water tight seal about the throat stoma comprises a sealing ridge.

7. A swimming apparatus as set forth in claim 6 wherein said ridge is disposed about the periphery of the throat stoma.

8. A swimming apparatus as set forth in claim 1 wherein said fastening means comprises strap means.

9. A swimming apparatus as set forth in claim 8 wherein said strap means comprises a neck strap and associated fastener.

10. A swimming apparatus as set forth in claim 9 wherein said strap means further comprises means for applying some downward force to the sealing member for holding the sealing member properly sealed.

11. A swimming apparatus as set forth in claim 10 wherein said downward force applying means comprises an arm strap coupled to the neck strap and adapted to extend under the arm.

12. A swimming apparatus as set forth in claim 1 wherein a water tight seal is provided only between the sealing member and the outer surface of the throat about the throat stoma.

13. A swimming apparatus as set forth in claim 1 wherein said seal forming means comprises a resilient rubberlike material employed as a seal secured to the inner surface of the sealing member and disposed between the sealing member and the throat.

14. A swimming apparatus as set forth in claim 1 wherein said sealing member is positioned against the external surface of the throat and is absent any structure to intrude into the throat stoma.

15. A swimming apparatus as set forth in claim 1 wherein said air chamber comprises front and rear pieces.

16. A swimming apparatus as set forth in claim 1 wherein the air chamber has a valve means for enabling introduction of air into the air chamber and enabling exit of air therefrom.

17. A swimming apparatus as set forth in claim 16 wherein said valve means is a flap valve.

18. A swimming apparatus used to enable a person having a laryngectomy or the like to safely swim, said apparatus comprising; an elongated unobstructed air tube, a mouthpiece means at one end of the air tube having an air passage communicating with the air tube to enable air passage between the air tube and the person's mouth, a relatively flat sealing member having means forming a water tight seal about the throat stoma, said sealing member also having an air passage means securing the other end of the air tube to the sealing member enabling air passage between the air tube and the person's throat, means holding the sealing member in water tight sealing relationship to the throat about the throat stoma, comprising both a fastening means coupled to the sealing member for securing the sealing member to the person and controllably inflatable air chamber means attached to the apparatus in front of and adjacent to the sealing member for maintaining the sealing member in a water tight position about the throat stoma, first valve means at the mouthpiece end of the air tube and operable during inhalation to permit air flow through the air tube to the throat stoma, and a second valve means disposed along the air tube and operable during exhalation for permitting air flow from the throat stoma therethrough.

19. A swimming apparatus as set forth in claim 18 wherein both said first and second valve means are one way valves.

20. A swimming apparatus as set forth in claim 18 wherein both said valve means comprise flap means.

* * * * *